(12) United States Patent
Mitsuhashi

(10) Patent No.: US 7,374,881 B2
(45) Date of Patent: May 20, 2008

(54) METHOD FOR COLLECTING AND USING NUCLEAR MRNA

(75) Inventor: Masato Mitsuhashi, Irvine, CA (US)

(73) Assignees: Hitachi Chemical Research Center, Inc., Irvine, CA (US); Hitachi Chemical Co., Ltd, Tokyo (JP)

(*) Notice: Subject to any disclaimer, the term of this patent is extended or adjusted under 35 U.S.C. 154(b) by 0 days.

(21) Appl. No.: 10/399,798

(22) PCT Filed: Oct. 25, 2001

(86) PCT No.: PCT/US01/49498

§ 371 (c)(1),
(2), (4) Date: Sep. 10, 2003

(87) PCT Pub. No.: WO02/066637

PCT Pub. Date: Aug. 29, 2002

(65) Prior Publication Data

US 2004/0072193 A1    Apr. 15, 2004

Related U.S. Application Data

(60) Provisional application No. 60/308,038, filed on Jul. 26, 2001, provisional application No. 60/244,672, filed on Oct. 31, 2000.

(51) Int. Cl.
*C12Q 1/68* (2006.01)
(52) U.S. Cl. ...................................................... 435/6
(58) Field of Classification Search .................... 435/6, 435/91.1, 91.2; 536/24.3, 23.1
See application file for complete search history.

(56) References Cited

U.S. PATENT DOCUMENTS

| | | | |
|---|---|---|---|
| 4,139,346 A * | 2/1979 | Rabbani | 422/56 |
| 4,430,278 A | 2/1984 | Jones, Sr. | |
| 4,906,561 A | 3/1990 | Thornthwaite | |
| 5,057,438 A | 10/1991 | Imai et al. | |
| 5,158,661 A | 10/1992 | Hansen | |
| 5,447,864 A * | 9/1995 | Raybuck et al. | 435/270 |
| 5,955,272 A * | 9/1999 | Lawrence et al. | 435/6 |
| 5,964,997 A | 10/1999 | McBride | |
| 5,990,298 A * | 11/1999 | Carmichael et al. | 536/24.1 |
| 6,113,763 A | 9/2000 | Henry et al. | |
| 6,264,814 B1 | 7/2001 | Lange | |
| 6,287,440 B1 | 9/2001 | Arnold et al. | |
| 6,319,379 B1 | 11/2001 | Davidson et al. | |
| 6,432,290 B1 | 8/2002 | Harrison et al. | |
| 6,495,319 B1 * | 12/2002 | McClelland et al. | 435/6 |
| 6,844,158 B1 | 1/2005 | Mitsuhashi | |
| 2002/0010323 A1 * | 1/2002 | Mitchell et al. | 536/23.1 |
| 2002/0039783 A1 * | 4/2002 | McMillan et al. | 435/287.2 |
| 2003/0152998 A1 | 8/2003 | Mitsuhashi | |
| 2004/0265864 A1 | 12/2004 | Mitsuhashi | |

FOREIGN PATENT DOCUMENTS

| | | |
|---|---|---|
| DE | 03715856 | 12/1988 |
| WO | WO 98 21321 | 5/1998 |
| WO | WO 99 32654 | 7/1999 |

OTHER PUBLICATIONS

Joklik. Procedures for studying transcription and translation of viral and host nucleic acids in interferon-treated cells. Methods in Enzymology. vol. 79, pp. 307-330, 1981.*
Hamaguchi et al. Direct reverse transcription-PCR on oligo(dT)-immobilized polypropylene microplates after capturing total mRNA from crude cell lysates. Clincal Chemistry, vol. 44, No. 11, pp. 2256-2263, 1998.*
Fukuchi et al. DNA damage induces p21 protein expression by inhibiting ubiquitination in ML-1 cells. Biochemica et Biophysica Acta. vol. 1404, pp. 405-411, 1998.*
Advanced Gene Computing Technologies Catalog, "RiboCap High Throughput RT-PCR System," p. 6, 1997.*
Mitsuhashi et al. Gene manipulation on plastic plates. Nature, vol. 357, pp. 519-520, 1992.*
Gribanov et al. Use of aerosol A-300 amd GF/F (GF/C) filters for purifying fragments of DNA, plasmid DNA, and RNA□□Biokhimiia. vol. 61, No. 6, pp. 1064-70, Jun. 1996, English language abstract only.*
retain. Thesaurus.com. Roget's New Millennium™ Thesaurus, First Edition (v 1.3.1), Lexico Publishing Group, LLC. http://thesaurus.reference.com/search?q=retain (accessed: Sep. 19, 2006).*
Advanced Gene Computing Technologies, Inc., RiboCap technical Sheet, p. 6, 1997.*
Millipore Corporation, Glass Fiber Filters Data Sheet, poages 1-4, Millipore Corporation, Bedford MA, Mar. 2001).*
Devary et al. Molecular and Cellular Biology, vol. 11, No. 5, pp. 2804-2811, May 1991.*
Matsuda K. et al. 2001 *High throughput methodology for measurement of newly expressed poly(A)+mRNA from nuclei* FASEB J 15:A515.
Derwent abstract of DE 03715856 A1 (Publ. Dec. 1, 1988).

\* cited by examiner

*Primary Examiner*—Gary Benzion
*Assistant Examiner*—Cynthia B. Wilder
(74) *Attorney, Agent, or Firm*—Knobbe Martens Olson & Bear LLP

(57) ABSTRACT

The present invention is related to a novel method of detecting mRNA, based on the fact that the newly synthesized mRNA is confined inside the cell nucleus. According to the novel method cells are captured on a membrane and then treated by a cell membrane permeation solution, thereby increasing permeability of cell membranes. After the cytoplasm is washed away, nuclei are dissolved with a cell dissolving solution, and then mRNA can be successfully recovered from the obtained solution.

20 Claims, 3 Drawing Sheets

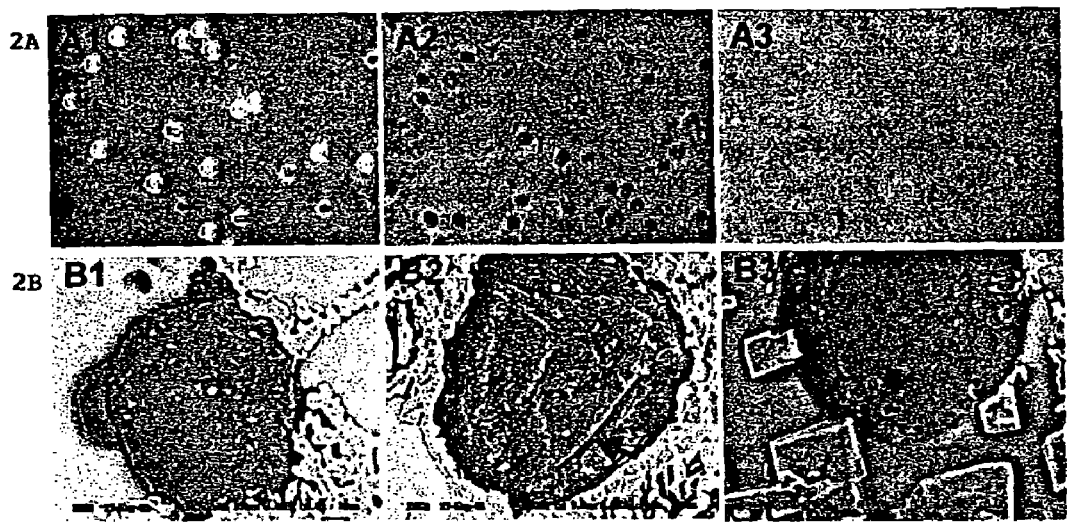
Fig. 2 Validation of nuclear mRNA extraction.

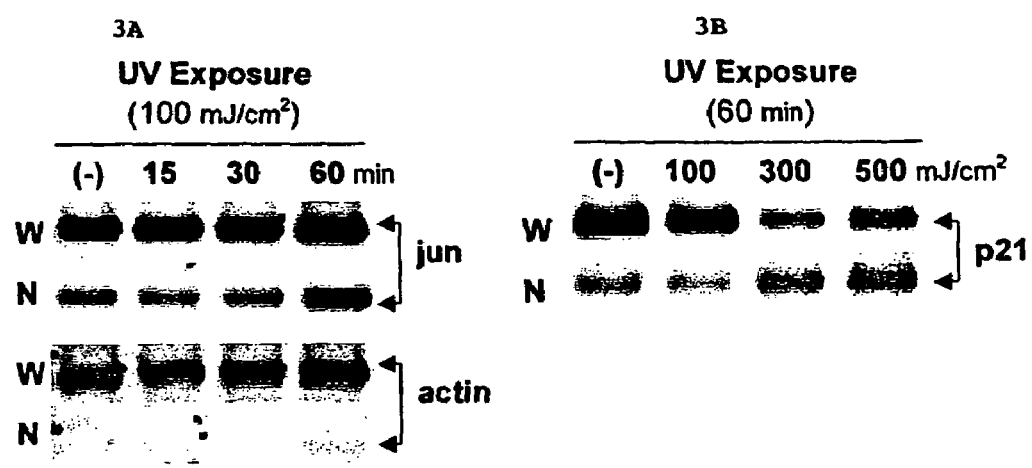
Fig. 3 Comparison of gene expression analysis between whole cell extraction and nuclear fraction.

METHOD FOR COLLECTING AND USING NUCLEAR MRNA

This is a U.S. National Phase under 35 U.S.C. §371 of International Application PCT/US01/49498, filed Oct. 25, 2001, which claims priority to U.S. Provisional Application No. 60/244,672, filed Oct. 31, 2000, and U.S. Provisional Application No. 60/308,038, filed Jul. 26, 2001, all of which are incorporated herein by reference in their entireties.

FIELD OF THE INVENTION

A method for isolating nuclear mRNA is disclosed. More specifically, the method involves capturing cells on a filter or membrane, permeabilizing the cells and isolating the nuclei. Then the nuclei are dissolved and the extract recovered.

BACKGROUND OF THE INVENTION

Conventional methods of isolation of mRNA isolate total mRNA from the cell. The mRNA isolated this way includes cytosolic mRNA and nuclear mRNA. For the purposes of quantitation and analysis of expression, it is important to only isolate the newly synthesized mRNA, not that which is being degraded in the cytoplasm. In this way one gets a "true" reading of the expression level or the changes in expression of a gene.

Gene expression analysis is of major interest in the field of functional genomics. Now that the human genome has been sequenced, there is a great need to identify genes and mutations which are involved in disease. These may be genes which are up- or down-regulated or genes which have polymorphisms. Many of the methods used to analyze these genes involve the isolation of mRNA. For example, DNA microarray chips can analyze the expression profile of thousands of different genes simultaneously. Reverse transcription polymerase chain reaction (RT-PCR) is a very sensitive method used to quantitate the expression of individual genes, and is rapidly replacing the more labor-intensive Northern blot analysis. There are many other non-PCR technologies available for sensitive gene detection, such as Nucleic Acid Sequence Based Amplification (NASBA), Strand Displacement Amplification (SDA), and branched DNA (bDNA) amplification.

Although many of these and other detection technologies have been developed and commercialized, the starting material is always total RNA or poly(A)+ RNA from cells or tissue samples. When total RNA or mRNA from a whole cell is used, the results are a mixture of the products of transcription as well as degradation products from the cytosol. This makes it difficult to detect expression of new mRNA under conditions that digestion of mRNA is in progress. Further, when a large amount of mRNA is already present, it is difficult to detect a slight change in the quantity of mRNA, and thus sensitivity is low.

The transcription of immature mRNA occurs in the nucleus, where poly(A) tails are attached and splicing occurs as needed. After this, the mature mRNA molecules then migrate into the cytoplasm and are translated and degraded. Since the amount of mRNA in the nucleus is directly related to the amount of transcription—not degradation—of mRNA, attempts have been made to purify the nuclear fraction in order to measure the amounts of specific mRNA (or nuclear RNA) in the nuclear fraction. Previous attempts to specifically analyze the nuclear fraction include the nuclear run-on assay which measures the level of transcription of specific genes. However, a major obstacle to the use of this assay is the amount of time required, the need for very careful handling to avoid ribonuclease contamination, and the generation of radioactive waste. Other techniques for purification of the nuclear fraction used time-consuming ultracentrifugation or labor-intensive microinjection to perform nuclear mRNA purification and analysis. These methods are not high throughput, and not suitable for precise quantitation. Moreover, it is not clear whether nuclear mRNA is preserved, for example, during the ultracentrifugation.

Thus, a rapid, sensitive, reliable, and high throughput methodology for isolation and analysis of the nuclear fraction of mRNA is needed. This would allow the analysis of "true" transcription levels of a gene.

SUMMARY OF THE INVENTION

In view of the above, in one aspect of the present invention, a method for the isolation of RNA from a cell is provided. The method comprises: (a) trapping cells on a filter or membrane; (b) permeabilizing the cells and isolating the nuclei; and (c) dissolving the nuclear membrane and recovering nuclear RNA, typically nuclear mRNA. In the above, at least the following embodiments may be included: the filter or membrane may be a glass fiber membrane; the permeabilizing may be by applying a mild detergent; the nuclei may be isolated by washing away the permeabilized cell membrane; the washing may be by vacuum filtration; the dissolving the nuclear membrane may be by lysis buffer; the lysis buffer may comprise a strong detergent; and the recovering the mRNA may be by transferring the permeabilized contents of the nuclei to a container for downstream RNA preparation, a filter or a column. The present invention can adopt the above embodiments singly or in a combination of two or more.

According to the above aspect of the present invention, expression of newly synthesized (transcribed) mRNA can be detected even under conditions that digestion of mRNA is in progress. The method is very simple, and only 2-3 minutes extra time is required as compared with conventional isolation methods, but a large amount of specimen can be treated. This method can easily be incorporated into an automated gene expression system.

In another aspect of the present invention, a method for the identification and/or quantitation of transcripts of a specific gene is provided. The method comprises: (a) obtaining the isolated mRNA using the aforesaid isolation method; (b) reverse transcribing the mRNA on said plate, filter or membrane; and (c) performing PCR using primers specific for the gene.

In another aspect, a method for the identification or quantitation of genes involved in the DNA repair process is provided. The method comprises: (a) treating cells with a DNA damaging agent; (b) obtaining the isolated mRNA of the aforesaid isolation method; (c) reverse transcribing the mRNA; and (d) identifying genes in which transcription has been up-regulated or activated by the DNA damage. In the above, in an embodiment, the identifying may be by a method selected from the group consisting of: RT-PCR, Northern blot, RAP PCR, ddPCR, subtraction, and array or genechip analysis.

The present invention can effectively be applied to the following method:

A method for detecting gene expression in a cell comprises: (a) trapping a cell on a filter or membrane; (b) contacting the cell with a cell membrane permeation solution to increase permeability of the cell membrane; (c)

washing the cytoplasm; (d) contacting the cytoplasm-washed cell with a cell dissolving solution to dissolve the nucleus, thereby obtaining a nuclear solution; (e) recovering mRNA from the nuclear solution; and (f) determining gene expression in the cell based on the quantity of the recovered mRNA. According to this aspect, a large scale processing can be realized with a high accuracy of gene expression even under conditions that digestion of mRNA is in progress.

In the above, at least the following embodiments may be included: the filter or membrane may be a glass fiber membrane; the cell membrane permeation solution may be a mild detergent which lyses the cell membrane but does not lyse the nucleus; the washing step may be conducted on the filter or membrane; the washing step may be conducted by vacuum filtration; the cell dissolving solution may be a lysis buffer which lyses the nucleus membrane; the lysis buffer may comprise a strong detergent; the mRNA recovery step may be conducted by transferring the permeabilized contents of the nucleus to an oligo dT-immobilized solid support; the solid support may be a plate, filter or column; the plate, filter or column may have a configuration such that the filter or membrane is fitted thereto; and the mRNA recovery step may be conducted by transferring the permeabilized contents of the nucleus to an oligonucleotides-immobilized solid support, said oligonucleotides having a sequence complimentary to the mRNA. The present invention can adopt the above embodiments singly or in a combination of two or more.

In still another aspect of the present invention, a method for determining gene expression in cells is provided. The method comprises: (i) collecting cells from a first biological sample; (ii) trapping the cells on a filter or membrane; (iii) contacting the cells with a cell membrane permeation solution to increase permeability of the cell membranes; (iv) washing the cytoplasm; (v) contacting the cytoplasm-washed cells with a cell dissolving solution to dissolve the nuclei, thereby obtaining a nuclear solution; (vi) recovering mRNA from the nuclear solution; (vii) repeating steps (i) through (vi) using cells from a second biological sample; and (viii) determining gene expression in the cells based on a change in the quantities of the specific species of mRNA recovered in steps (vi) and (vii), respectively. In the above, in one embodiment, a designated treatment may have been applied to the second sample, not the first sample. This method can effectively be used for determination of the efficacy of candidate chemicals for a designated purpose.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

FIGS. 2(A-E) show validation that the mRNA extracted in the preferred embodiment of the invention is nuclear mRNA. FIG. 2A shows light microscopy, FIG. 2B shows scanning electron microscopy (SEM), FIG. 2C shows agarose gel electrophoresis. In FIGS. 2C and 2D, the purified nuclear materials shown in FIG. 2C were used to amplify mitochondrial DNA by 20 cycles of PCR, and to perform PCR (FIG. 2D).

FIG. 3 is a Comparison of gene expression analysis between whole cell extraction of mRNA and the nuclear fraction of mRNA. FIG. 3A shows amplification of junB and β-actin after UV-treatment. FIG. 3B shows amplification of p21 after UV-treatment of the cells.

DETAILED DESCRIPTION OF THE PREFERRED EMBODIMENT

Figure 1:
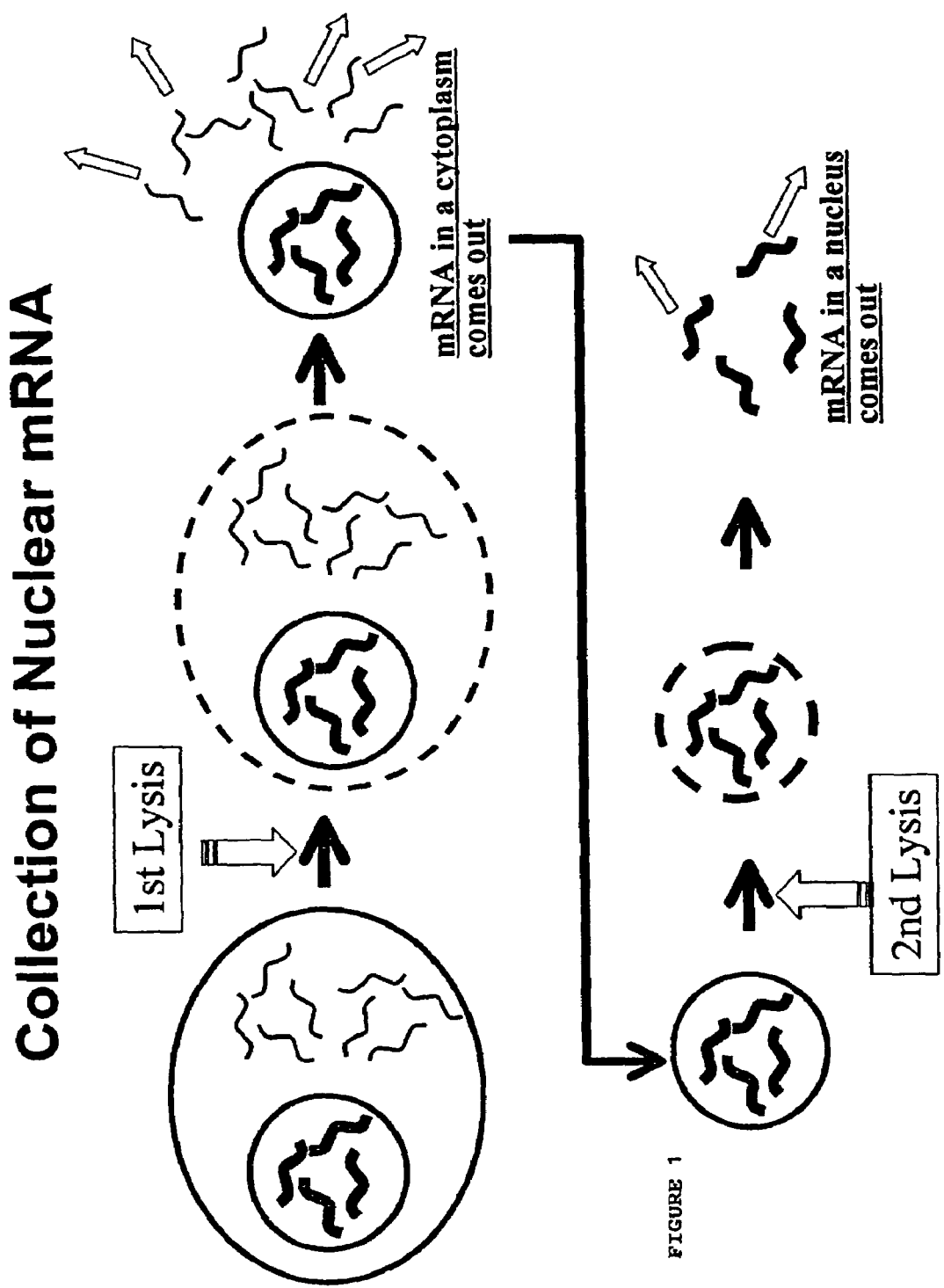
FIG. 1 is a pictorial diagram showing an outline of the preferred embodiment of the invention.

A fast, simple method for isolating nuclear mRNA is disclosed which involves capturing cells on a solid support, permeabilizing the cells and isolating the nuclei. The nuclei are dissolved and the extract containing nuclear mRNA is recovered. The method allows for high throughput purification and analysis of the "true" expression levels of a gene. The method also allows for identifying small changes in gene expression without the interference of degradation products.

With reference to FIG. 1, the first lysis in the procedure is a mild lysis which allows for the removal of the cell membrane and cytoplasm (including mitochondria and mRNA degradation products, tRNA, and rRNA) while leaving the nucleus (containing the newly synthesized mRNA) intact. A mild detergent may be used in order to lyse the cell but not the nucleus. Examples of detergents which can be used include but are not limited to: NP-40, Triton-X 100, and Saponin. The mild detergent remains on the cells for a time long enough to permeabilize the cell without vigorous mixing. Use of the mild detergent for a short time allows the cells to be permeabilized without lysing or permeabilizing the nuclear membrane, in fact there is little or no damage to the nuclei. In addition, the method allows for the exposure of the solution to all of the cells which results in a better yield of mRNA and RNase inactivation is not necessary.

The next step involves lysis of the nucleus typically using a strong detergent for a time long enough to lyse the nucleus. Gentle mixing may be used to expose all of the nuclei to the lysis solution and to inactivate RNases, however, this is not believed necessary and may not be beneficial, in fact it may reduce the yield.

The resulting mRNA can be used for any method which requires mRNA, however, the presently disclosed method is particularly advantageous for analysis of the expression of a gene. This is because, the mRNA that is being analyzed is that mRNA which is newly synthesized within the nucleus. Typically, methods of purification of mRNA use total mRNA which includes any degradation products found in the cytoplasm. Thus, the present method is particularly advantageous for analyzing transcripts produced by a gene under different cellular conditions. The size of the transcripts as well as the level can be more accurately identified.

Uses for the mRNA produced by the method of the preferred embodiment include any methods which seek to analyze mRNA expression. These include, but are not limited to: PCR, cDNA library production and analysis, analysis of genechips and microarrays, ddPCR (and other comparable techniques), and quantitative PCR.

Before the lysis procedure, the cells are applied to a solid support. The solid support may allow attachment of the cells by charge, covalently, or hydrophobically or may just provide a support for the cells. Examples of solid supports include membranes, filters, glass plates, paper, plastic, beads, fibrous polyester and columns. The choice of which solid support to use may depend on the purpose for the mRNA. For example, if the mRNA is going to be fluorescently labeled and analyzed by fluorescent microscopy, a glass slide may be used. If the mRNA is going to be used for quantitative PCR, a microwell plate with filters may be used, alternatively a chip or array may be used.

Initial Cellular Lysis

The initial lysis can be with any material, reagent, or buffer which permeabilizes or removes the cytoplasmic membrane, but does not lyse the nuclei. It may be advantageous for the cytoplasm to remain in contact with the nucleus during the lysis procedure to help protect the nucleus. Examples of buffers which may be used for the lysis include, but are not limited to, buffers containing mild detergents, PBS, or Hank's balanced salt solution. Typically, because the first lysis is mild, there is little or no mixing. If the cells possess a cell wall in addition to a cell membrane, additional steps may be required to remove the cell wall before or at the same time as the cell membrane. For Prokaryotic cells, the nuclear lysis is not necessary and the initial lysis with or without the removal of the cell wall is sufficient.

Cell Wall Removal

If necessary, the cell wall is removed at the same time as or before the initial lysis. Animal cells, insect cells, and protozoa typically do not possess a cell wall. Therefore, they do not require an initial treatment to remove a cell wall or cell wall type structure. However, most bacteria possess a cell wall comprising peptidoglycan. Fungi possess a cell wall comprising cellulose or chitin, and Plants possess a cell wall comprising cellulose, lignin, pectin and/or keratin. However, methods of removal of cell walls while leaving the cell membrane intact have been known and used for decades. These methods produce variants which may be referred to as spheroplasts, protoplasts, or L forms. An overview of the methods are described below. However, such methods can be identified by one of skill in the art.

Among the bacteria, there are a variety of cell wall types and they range from no cell wall (mycoplasma) to a very strong protective structure which is difficult to destroy referred to as the endospore. The cell walls of Eubacteria are often designated as Gram positive or Gram negative, referring to the cell's reaction to treatment with various stains. The Gram positive bacteria possess only the peptidoglycan layer and a cell membrane, while Gram negative bacteria possess an outer membrane, a cell wall with peptidoglycan and an inner membrane. Acid fast bacteria such as the Mycobacteria typically contain a lipid component to the cell wall. Each cell wall requires a slightly different treatment to remove. However, there are methods for removal of all types of cell walls.

Methods of removal of the cell wall from bacteria producing L forms, spheroplasts, and protoplasts have been known for many years. The methods typically involve the use of an enzyme to break down the cell wall components and a buffer system which allows for osmotic stability of the resulting cell, now without a cell wall. Alternatively, bacteria are grown in a medium containing an antibiotic which breaks down the cell wall and the medium allows for osmotic stability of the resulting L-forms, spheroplasts or protoplasts. Enzymes which have been used include but are not limited to: lysozyme. Antibiotics which have been used include but are not limited to: penicillins such as ampicillin (10×MIC in Hornsten, E G, et al. Diagn. Microbiol Infect Dis 1989 March-April; 12(2):171-5) and Globomycin (Inukai M., et al. J. Antibiot (Tokyo) 1978 May;31(5):410-20).

If the bacteria additionally contains a capsule, methods are known in the art for removal of the capsule and include the use of water and PBS with an incubation of 1 hour at various temperatures (Gentry, et al. Am J. Vet. Res. 1982 November;43(11):2070-3). The standard technique for production of spheroplasts from gram negative bacteria including *Gluconobacter, Acetobacter, Erwinia, Pseudomonas,* and *Corynebacterium* involves Tris-sucrose-EDTA-lysozyme (Verma, V. et al. Biotechniques 1989 May;7(5): 449.52). Gram positive bacteria such as *Bacillus* and *Clostridia* may require a somewhat stronger treatment to produce protoplasts (Jacobson, ED, et al. J. Bacteriol. 1975 October;124(1):445.8; and Durban E. et al. Can J. Microbiol 1974 March;20(3):353-8). Spheroplasts may also be formed for plague bacteria (*Yersinia*) by the use of lithium chloride (Gramotina L I., et al. Antibiotiki 1977 July;22(7):634-9). Other methods for gram negative bacteria such as *E. coli* use lysozyme and EDTA (Birdsell D. C., et al. J. Bacteriol 1967 January;93(1):427-37). *Agrobacterium* require a slightly different method (Beardsley, et al. Cancer Res. 1966 August; 26(8):1606-10) and *Streptomyces* produce spheroplasts in liquid medium supplemented with lysozyme and penicillin (Innes C. M., et al. J. Appl. Microbiol. 2001 March;90(3): 301-8).

Fungi possess a cell wall comprising chitin and/or cellulose. Typically enzymes are used to remove the cell wall and the process is conducted in a medium or buffer which allows for osmotic stability. Enzymes used to remove the cell wall include, but are not limited to: cellulases and chitinases (Masuda, S. et al. Biosci Biotechnol Biochem 2001 August; 65(8):1883-5). Yeast are a type of fungi with a variant type of cell wall. Yeast cells can produce spheroplasts using a mixture of a reducing agent and 1,3 beta-glucanase isolated from *Basidiomycete* or a comparable enzyme (Havelkova, M. Arch Mikrobiol 1973 Mar. 2;90(1):77-88). This method can be used for Ascomycetes and some fungi imperfecti. Other fungi required the addition of a second enzyme, 1,4-alpha-glucanase.

Protozoa, such as amoeba contain no cell wall. Paramecium, plasmodium, giardia, and other protozoa may posses a pellicle. Protozoa such as *Neurospora* can be made to produce spheroplasts even with a pellicle (Scarborough G A., et al. Anal Biochem 1974 October;61(2):441-7).

Plant cells have strong cell walls which may contain one or more of the following: pectin, lignin, and keratin. Thus, to produce spheroplasts, enzymes which can break down the cell wall components are used in a medium which allows for osmotic stability. Typical enzymes used include, but are not limited to: ligninases, pectinases and keratinases (Levit, M. N., et. al. Bioorg Khim 1992 March:18(3):309-45).

Isolation of Single Cells From Tissue

For the method disclosed herein, single cells are typically used. Thus, when cells from a tissue biopsy or an organ are used, the extracellular matrix is typically removed and the cells separated before application to the membrane for the first lysis. The technique of removal of the extracellular matrix and isolation of cells from one another has been known and is used in the process of tissue culture. It may involve the used of EDTA and trypsin. Alternatively, any enzymes or buffers which cause dissociation of the tissue and intercellular matrix are used, including but not limited to collagenase.

Final Nuclear Lysis

The nuclear lysis step may take place on the original solid support, or alternatively, the nuclei may be moved to a second support, such as a membrane which specifically binds mRNA, RNA, DNA, or any mixture thereof. However, typically the nuclei are not moved because although they are intact they may be fragile and the process of moving them may decrease the yield of mRNA.

The nucleus may be lysed by any method which allows for permeabilization and lysis of the nucleus without damage to the mRNA. Typically, a detergent may be used with vigorous mixing to allow the complete lysis of all of the nuclei. Detergents usable with the method include, but are not limited to: NP-40, SDS, and triton-X. Other buffers or reagents which can be use include: lysis buffer from Invitrogen's Fast track kit. Or a buffer with the following basic components or equivalents thereof: buffer to maintain pH, salt to maintain the hybridization stringency between the oligo-dT and the polyA tail, detergent to lyse the membrane, DNase and/or RNase inhibitors including proteinase K, guanidine, RNasin may be used.

The nuclear extract or nucleoplasm may then be removed and the mRNA fraction isolated in a variety of ways. The fraction may be applied to an mRNA-specific membrane, column, or bead. For example, an oligo-(dT) membrane, column or filter will allow for the purification of the mRNA from the nucleoplasm. Alternatively, DNases, and phenol or equivalents thereof can be used to remove proteins and DNA.

In a preferred embodiment, a 96 well-GFIC glass fiber filter plate (e.g., the RIBOCAP™ filterplate, RNAture, CA) is used for the method. Any filter plate which can capture cells and can support the nucleus after treating the cells with a mild detergent can be used. The filter plate initially contains a glassfiber filter membrane which is used as the solid support for the cells. The cytoplasm and cell membrane or cell wall components are washed away by use of vacuum filtration. In this way washes may be performed with minimal loss of nuclear mRNA. This also allows for a very simple, high throughput method.

In a further preferred embodiment, an oligo-(dT) plate can be used (e.g., GENEPLATE™ mRNA plate, RNAture, CA) to capture the mRNA. GenePlatem is a microtiter plate to which oligo-(dT) sequences have been immobilized covalently. It allows for quantitation to be easily performed by adding a fluorescent indicator dye (Yoyo-1). The apparatus and quantitation method are described in U.S. patent application Ser. No. 08/772,150, filed Dec. 20, 1996 (herein incorporated by reference). If a specific sequence is immobilized on a microtiter plate, mRNA having a sequence complimentary to the sequence can be captured. In the above, preferably, the filter plate can be fitted to the microtiter plate, both of which have the same number of wells, so that filtering and capturing can be conducted continuously.

An analysis of the method described herein as compared to a conventional method is presented in Table I. It is clear from this analysis that the method can easily be converted to high throughput and even automated technology, while conventional methods are too cumbersome and time-consuming for such an application.

TABLE I

Comparison of the method herein and a conventional method

|  | Method herein | Conventional method |
| --- | --- | --- |
| Location of cell trap | Membranes | Tubes |
| Method of trap | Vacuum or low speed centrifugation | Ultra-centrifugation |
| Wash after first lysis | Easy and fast | Time consuming |
| vortex | no | Required (degree of vortex may influence the results due to the mechanical damage to nuclei) |
| Throughput | 96 samples per assay | Dependent on the type of rotor of ultra-centrifuge |
| Potential automation | easy | difficult |

Application of the Method

The method can be applied to the analysis of genechips and microarrays, diagnostic analysis by PCR, production of cDNA libraries, Northern blots, and differential display or subtraction library techniques. It is particularly advantageous because when identifying a gene or isolating alternative transcripts of a gene, the degradation products of mRNA can provide erroneous results, such as smaller transcripts which only exist as degradation products.

In the following examples, the method is analyzed and the resulting mRNA tested for contamination by mitochondrial RNA (cytoplasmic components). The quality of the resulting nuclear mRNA is tested by PCR of -actin. Finally the quality of the resultant nuclear mRNA is tested by performing an experiment in which cells are irradiated with UV light and the levels of two known gene products, p21 and junB are tested.

EXAMPLES

The method used and analyzed in the following examples involves trapping cells on a glass fiber GF/C membrane, washing with a buffer, and removing the wash with a method such as vacuum, positive pressure, or centrifugation for example. In one embodiment, the cells were incubated with the first lysis buffer, the cytosolic fraction was released by vacuum, positive pressure, or centrifugation, and the cytosolic fraction was washed away with PBS 2-3 times to remove the cytosolic mRNA. The second lysis buffer was applied and incubated for a time long enough to lyse the nuclei. The second lysis buffer was released by vacuum, positive pressure, or centrifugation, revealing the nuclear fraction.

The method was advantageously adapted to use the RIBOCAP™ filterplate and GENEPLATE™ mRNA plate from RNAture to make the method high throughput and allow for automation. Thus, the following Examples outline the adaptation to the RIBOCAP™ filterplate and GENEPLATE™ mRNA plate from RNAture and the level of purification was analyzed. The cells, apparatus, and buffers were as follows: human histiocytic cell line, U937, a human erythroleukemia cell line, K562, jun-B plasmid (ATCC, Manassas, Va., USA), RIBOCAP™ filterplate, GENEPLATE™ mRNA plate, WASH BUFFER, LYSIS BUFFER (RNAture, Irvine, Calif.).

Example 1

Isolation of Nuclei Using the RIBOCAP™ Filterplate

The RIBOCAP™ filterplate was used for capturing the cells. (RNAture, Irvine, Calif.). RIBOCAP™ filterplate is a 96-well plate with a glassfiber filter membrane attached at the bottom. The cells were applied to the RIBOCAP™ filterplate, and were trapped on the membrane by vacuum filtration. A mild detergent, NP-40, was added to the RIBOCAP™ filterplate to permeate the cells. In order to avoid direct exposure of high concentrations of NP-40 to the nuclear membrane, cells were exposed to NP-40 on the RIBOCAP™ filterplate filter membrane without agitation or vortexing. The cytosolic components were still present in the cells even after the NP-40 treatment, and may have protected the nuclei from potential damage. The flow-through fraction was occasionally examined under a microscope and intact cells were never found in this fraction. In addition, because the wash solution, PBS, did not contain NP-40, the nuclei were protected while the cytoplasmic components were removed by washing. This mild lysis procedure in combination with the RIBOCAP™ filterplate allowed for highly reproducible data.

The nucleus was then lysed and the mRNA captured onto the GENEPLATE™ mRNA plate as in Example 2.

Example 2

Isolation of mRNA from the Nucleus Using a Poly dT Filter Plate (Geneplate)

The GENEPLATE mRNA plate (RNAture) was advantageously manufactured to fit over the RiboCap filter plate. Thus, after lysis of the nuclei in the RIBOCAP™ filterplate plate, the mRNA was collected in the GENEPLATE mRNA plate by setting the RIBOCAP™ filterplate plate over the GENEPLATE mRNA plate and using vacuum pressure to transfer the nucleoplasm containing the mRNA. After the mRNA and nuclear contents were collected on the GenePlate, the mRNA was allowed to bind and the washes were performed to remove the nuclear contents as follows:

The nuclear components of the nuclei were released using 50 μl of LYSIS BUFFER (RNAture) with 1% 2-mercaptoethanol, which was applied to the wells of the RIBOCAP™ filterplate, and incubated at room temperature for 15 min. The lysate was then transferred from the RIBOCAP™ filterplate to the microplate containing the poly-(dT) by centrifugation at 3,200×g at 4° C. for 5 min, which in some cases was followed by two rounds of phenol/chloroform/isoamyl alcohol extraction and ethanol precipitation (FIGS. 2C and 2D). In FIGS. 2A and 2B no phenol/chloroform/isoamyl alcohol extraction and ethanol precipitation was performed.

In Examples 3 and 4 the method was verified.

Example 3

Verification of Cell Lysis by Light Microscopy and SEM

To verify cellular and nuclear lysis, the method was performed as follows: U937 cells were applied to the RIBOCAP™ filterplate, and trapped onto the glassfiber membrane (GENEPLATE mRNA plate ) by vacuum with 4 inches of Hg. To remove the cytosolic components, 100 μL 0.1% of NP-40 was applied to the wells, and incubated at room temperature for 0, 5, 15, 30, and 60 sec. Then, the RIBOCAP™ filterplate was washed with 100 μL PBS three times. To release the nuclear components from the nuclei, 50 μL LYSIS BUFFER (RNAture) with 1% 2-mercaptoethanol was applied to the wells of the RIBOCAP™ filterplate, and incubated at room temperature for 15 min. The lysate was then transferred from the RIBOCAP™ filterplate to a microplate by centrifugation at 3,200×g at 40° C. for 5 min, followed by two rounds of phenol/chloroform/isoamyl alcohol extraction and ethanol precipitation.

Light microscopy performed on the U937 cells showed that the cells were still intact. The results in FIG. 2A include: a negative control (untreated U937 cells, A1), the same cells after a 1 minute exposure to 0.1% NP-40 stained with trypan blue (A2), and the same cells after exposure to LYSIS BUFFER (A3). As shown in FIGS. 2A1-2, NP-40-induced cell permeation was confirmed by trypan blue staining. Interestingly, the cell shape was almost intact even after a 15 min exposure to NP-40 (FIG. 2A2).

In order to visualize the damage to the cell membrane, cell surface characteristics were analyzed by scanning electron microscope (SEM). Since conventional SEM requires a strong vacuum, it is difficult to visualize the native condition of cell surfaces. Therefore, the newest model of weak vacuum SEM (Hitachi S3000N) was used. Scanning EM was performed as follows: Cells (U937 and K562) were resuspended in 10 mM Tris, pH 7.4, and spread onto a glass slide, and inserted into a Hitachi S3000N (Nissei Sangyo America, Pleasanton, Calif., USA) SEM with a vacuum of 60-70 Pa and an accelerating voltage of 5 KV. Sub-signal BSE2 images were used for photographic recording. FIG. 2B shows SEM (scanning electron microscopy) of K562 cells untreated (x5,000 B 1) and treated with a 30 second exposure to 0.1% NP-40. Accelerating voltage was 5 KV, and vacuum pressure was 60 (B3) or 70 (B 1-2) pa.

Although crystals of salt were observed, even in a weak vacuum condition, some cells were present in the salt-free area with the cell surface clearly exposed (FIG. 2B1-3). Crevasses (FIG. 2B2) and holes (FIG. 2B3) were observed on the cell membranes of NP-40 treated cells (see arrows). This damage was mild enough to maintain intact nuclei within the cells, while perforating the cell membrane.

In Example 4, the nucleus was lysed and lysis verified.

Example 4

Verification of Nuclear Lysis

After lysis of the cells as in Example 3, the filter plate was washed with PBS three times to remove the cytosolic components. The flow-through fraction was observed by microscope, but no nuclei were observed in this fraction, suggesting that the nuclei were still trapped on the glass fiber membrane of the RIBOCAP™ filterplate. Then, LYSIS BUFFER was applied to the RIBOCAP™ filterplate to break up the nuclear membrane. Complete lysis of cells was confirmed by light microscopy. The nuclear lysate was then treated with 2 rounds of extraction by phenol/chloroform/isoamyl alcohol followed by ethanol precipitation.

In Examples 5-10, the nucleic acid was analyzed by agarose gel and PCR.

Example 6

Analysis of the Purified Nucleic Acid by Agarose Gel Electrophoresis

In order to confirm that the cytosolic components were removed, the purified nucleic acid materials were analyzed by agarose gel electrophoresis. The method was performed as follows: U937 Cells ($5.0 \times 10^5$ cells/well) were applied to the RIBOCAP™ filterplate (RNAture), and trapped onto the glassfiber membrane by vacuum with 4 inch Hg. To remove the cytosolic components, 100 mL 0.1% of NP-40 (Sigma, St Louis, Mo., USA) was applied onto the well, and incubated at room temperature for 5-60 sec. Then, the RIBOCAP™ filterplate was washed with 100 µL PBS three times. To release the nuclear components from the nuclei, 50 µL LYSIS BUFFER (RNAture) with 1% 2-mercaptoethanol (Bio-Rad, Hercules, Calif., USA) was applied to the wells of the RiboCap.TM. filterplate, and incubated at room temperature for 15 min. The lysate was then transferred from the RIBOCAP™ filterplate to a microplate by centrifugation at 3,200.xg at 4° C. for 5 min, followed by two rounds of phenol/chloroform/isoamyl alcohol extraction and ethanol precipitation.

For electrophoresis, purified nucleic acid materials were denatured by 3.7% formaldehyde and analyzed by 1.25% agarose gel electrophoresis, stained with SYBRGOLD (Molecular Probes, Eugene, Oreg., USA), and recorded by a fluorescent scanner (FM-BIO-II, Hitachi Genetic System, Alameda, Calif., USA). As shown in FIG. 2C, the 18s- and 28s-rRNA bands (indicated by lower 2 arrows) were reduced after NP-40 treatment, whereas the DNA (top arrow) was unchanged (MK: molecular weight marker).

The resulting nucleic acid materials were also analyzed by PCR.

Example 6

PCR of Mitochondrial DNA

Since agarose gel electrophoresis is not quantitative, the level of mitochondrial DNA (mtDNA) was measured by PCR. Because mitochondria exist only in the cytosol, this provided a measure of the cytosolic components which still existed. The resulting nucleic acid from Example 3 was used for PCR for mitochondrial DNA (mt DNA) amplification. Twenty µL of premixed PCR buffer (0.25 µmol/L each of primers, 1×PCR buffer, 2.5 µmol/L $MgCl_2$, 100 .mu.mol/L each of dATP, dGTP, dCTP and dTTP, 1 unit of Taq Polymerase), and one drop of mineral oil (Sigma) was added to each well, and amplification was performed with denaturation at 94° C. for 1 min, annealing at 56° C. for 1 min, followed by extension at 72° C. for 1 min for 20 cycles in a thermal cycler (UNO 11, Biometra, Horsham, Pa., USA). PCR products were analyzed by 2% agarose gel electrophoresis, stained with ethidium bromide (Sigma), and recorded by a photographic detection (Alphalmager 2200, Alpha Innotech, San Leandro, Calif., USA). The primers for mitochondrial DNA (mtDNA) were 5'-TCCACACTAGCA-GAGACCAACCG-3' (SEQ ID NO:1) and, 5' AGAA-CAGGGAGGTTAGAAGTAGGGT-3' (SEQ ID NO:2) were designed by the computer program HYBSIMULATOR™ (RNAture) with hybridization simulation against a GenBank UniGene database to eliminate non-specific hybridization.

As shown in FIG. 2D, mitochondrial DNA (mtDNA) was amplified in whole cell extracts before NP-40 treatment, however, after more than a 15 sec exposure to NP-40, the amount of mtDNA PCR product was reduced substantially (FIG. 2D). This indicated that the cytosolic components were reduced during NP-40 treatment and subsequent washing procedures. By quantitating the amount of PCR product of mtDNA before and after NP-40 treatment, the purity of the nuclear fraction was calculated.

Example 8

BT-PCR of Nuclear mRNA

The nuclear lysates (from Example 3) were directly transferred from the RIBOCAP™ filterplate to the GENEPLATE mRNA plate, and incubated at room temperature for 1 hr for hybridization. The GENEPLATE mRNA plate was then washed with 50 µL LYSIS BUFFER twice, followed by two washes with 50 µL WASH BUFFER (RNAture). The cDNA was synthesized in the GENEPLATE™ mRNA plate using the immobilized oligo(dT) as a primer, by adding 20 µL of premixed cDNA buffer (1×RT buffer, 500 µmol/L each of dATP, dGTP, dCTP and dTTP, 100 units of MMLV reverse transcriptase).

Example 9

PCR of -Actin

Agarose gel electrophoresis and mtDNA PCR do not provide any quantitative data for the intactness of the nucleus during NP-40 treatment and subsequent washing procedures. Therefore, because immature mRNA exists mainly in the nucleus, the amount of pre-splicing immature β-actin mRNA was measured by RT-PCR. The crude nuclear lysate was directly transferred from the RIBOCAP™ filterplate to the oligo(dT)-immobilized PCR microplate by centrifugation. Because the LYSIS BUFFER has an optimized stringency for hybridization between oligo(dT) and poly(A) tails of mRNA, and contains strong detergent to inactivate RNase activities, mRNA can be captured by GENE-PLATE™ mRNA plate during room temperature incubation for 1 hr. After non-hybridized materials were removed by washing each well with WASH BUFFER, cDNA was synthesized in the same plate using the immobilized oligo(dT) as a primer.

Although the GENEPLATE™ mRNA plate selectively captures mRNA, not DNA, it was not clear whether the PCR products were derived from mRNA or contaminated nuclear DNA. Non-specifically bound DNA can be removed by extensive washing after hybridization. However, this process also dissociates some mRNA, which will decrease the sensitivity and reproducibility. Therefore, because cDNA is covalently immobilized to the GENEPLATE™ mRNA plate via immobilized oligo(dT), each well was washed extensively after cDNA was synthesized. After each well was washed with 10 mM Tris, pH 7.4, five times, PCR was conducted. RT-PCR was conducted as in Example 5 and PCR was conducted to amplify the intron portion of β-actin as follows: PCR was conducted for 20 to 50 cycles with MMLV reverse transcriptase (GIBCO/BRL, Rockville, Md., USA), PCR reagents (Promega, Madison, Wis., USA), and dNTP's (Yamasa, Tokyo, Japan).

The primers for β-actin 5'-TGGCACCACACCTTCTA-CAA 3' (SEQ ID NO:3), and 5'-CATCTCTTGCTC-GAAGTCCA-3') (SEQ ID NO:4), and β-actin intron (5'-GTGCTGTGGAAGCTAAGTCCTGC-3' (SEQ ID NO:5), and 5'-CACCCACCTTGATCTTCATTGTGCT-3') (SEQ ID NO:6) were designed by the computer program HYBSIMU- LATOR™ (RNAture) with hybridization simulation against a GenBank UniGene database to eliminate non-specific hybridization.

The PCR was then compared with or without cDNA synthesis. As shown in FIG. 2E, the β-actin intron was not amplified without cDNA synthesis (RT−), whereas it was successfully amplified with cDNA synthesis (RT+). Furthermore, as shown in FIG. 2E, the band intensity of β-actin intron PCR products were unchanged during NP-40 treatment. In separate experiments, it was confirmed that the band intensity of FIG. 2E was not saturated and existed in the dynamic range of quantitation. This suggests that the amount of β-actin intron was well preserved during NP-40 treatment.

In order to test the procedure for analysis of the up and down-regulation of a gene the effect of UV irradiation on the expression of jun-B was analyzed.

Example 10

Analysis of Jun-B and p21 Expression and Induction by UVC

U937 cells were grown in RPMI-1640 containing 100 mill fetal bovine serum, 500,000 units/L penicillin, and 500 mg/L streptomycin (phosphate buffered saline (PBS), cell culture media, antibiotics, and fetal bovine serum purchased from GIBCO/BRL, Rockville, Md., USA). Cell viability was assessed by the exclusion of trypan blue and was always >95%. Cells were resuspended in the above media without phenol red at a concentration of 104 cells/μL, and 100 μL of cell suspension was applied to the well of a 96-well culture plate. The plate was then placed in the STRATALINKER 1800 (Stratagene, La Jolla, Calif., USA) and exposed to UVC (254 nm) at a fluence of 100, 300, and 500 $mJ/cm^2$. Cells were trapped on the glassfiber membrane of the RIBOCAP™ filterplate by centrifugation. For the whole cell assay (W), LYSIS BUFFER was applied to the RIBOCAP™ filterplate, and lysates were transferred to a GenePlates for poly(A)+ RNA capture. For nuclear analysis (N), the RIBOCAP™ filterplate was treated with 0.1% NP-40 for 60 sec, and immediately washed with PBS. Then the LYSIS BUFFER was applied and the same protocol as used for the whole cell assay was used. After mRNA was captured by GENEPLATE™ mRNA plate, cDNA was synthesized, followed by PCR to amplify jun-B (30 cycles), .beta.-actin (35 cycles), and p21 (30 cycles for W, 44 cycles for N). The primers for jun-B (5'-AGGACAAGGTGAAGACGCTCAAGG-3' (SEQ ID NO:7),and 5'-GCAGGGGACGTTCAGAAGGC-3') (SEQ ID NO:8), and the primers for p21 (5'-CCGCTCTACATCTTCTGCCTTAGT-3' (SEQ ID NO:9),and 5'-CAGCACTCTTAGGAACCTCTCATTCAAC-3') (SEQ ID NO:10) were designed by the computer program HYBSIMULATOR™ (RNAture) with hybridization simulation against a GenBank UniGene database to eliminate non-specific hybridization. See Example 9 for -actin primers.

This method was first used to confirm ultraviolet (UVC)-induced jun-B expression. The doses of UVC used in this experiment (100, 300, and 500 $mJ/cm^2$) were very high compared to other reports. However, because the cells were exposed to UVC, in 100 μL PBS in a 96-well plate, the viability was always above 95% by trypan-blue examination, even 24 hrs after radiation. As shown in FIG. 2A, high background expression of jun-B was observed in whole cells (W), which masked the UVC-induced increase in jun-B expression. When the cytosolic fraction was removed by NP-40 treatment, the background jun-B expression was reduced substantially, and UVC-induced jun-B expression was clearly observed in the nuclear fraction (N). Interestingly, jun-B was also expressed weakly in the nuclear fraction before UVC stimulation, which may represent a metabolic level of Jun-B in U937 cells. Because both the whole cell extract and the nuclear fraction were analyzed simultaneously under identical conditions, the difference in the band intensity may indicate the amounts of the cytosolic Jun-B mRNA. The control β-actin was also amplified from the whole cell extract, but no change was detected before and after UVC stimulation (FIG. 2A). Interestingly, β-actin was not detected in the nuclear fractions even after UVC stimulation, suggesting lower metabolic levels of β-actin mRNA than that of jun-B in this cell line.

Because of the somewhat surprising results of up-regulation and down-regulation of jun-B by UVC stimulation, p21 gene expression was analyzed in whole cell extracts of U937 cells. The levels of p21 (FIG. 2B) were reduced after more than 300 $mJ/cm^2$ UV exposure. However, once the cytosolic fraction was removed, p21 expression was significantly increased after UVC exposure in the nuclear fraction (FIG. 3B). These results suggest that the UV exposure to U937 cells may increase not only their p21 transcription but also degradation.

Example 11

Use of the Method for Diagnostic Analysis by PCR

Single Nucleotide Polymorphisms (SNPs) are typically identified in a patient sample by RTPCR with or without hybridization. Thus, blood cells from a patient are used to isolate nuclear mRNA as in Examples 1-4. The mRNA is reversed transcribed using SNP-specific primers and the SNP identified.

In this way, the SNP associated with Type 2B von Willebrand's disease is identified in a patient who presents with symptoms. White blood cells from the patient were isolated and used to isolate nuclear mRNA as in Examples 1-4. The mRNA was used for RTPCR using primers between amino acids 510 and 600 of the vWF gene exon 28 (Wood, N. et al. Thrombosis and Haemostasis, 1996, 75(2) 363-7):

The primers used are capable of identifying the following SNPs which are associated with Type 2B van Willebrand's disease (two 3 base deletions in codons 544 and 551/552 and 2 two base substitutions in codons 574/575 and 577/578). The patient is found to have the 3 base deletion in amino acid 544.

Example 12

Use of the Method for Microarray Analysis

Genechips and Microarrays are quickly changing the way researchers think about gene expression. Instead of studying one gene at a time, experiments can elucidate the gene expression profiles of thousands of genes simultaneously. The microarays are typically produced by spotting labeled cDNA or labeled cRNA. Then, the analysis is accomplished by hybridizing with labeled cDNA from a diseased compared to a normal tissue. However, if the cDNA is produced from total RNA or mRNA from cells or tissues, the results will be imprecise or even incorrect. Thus, a microarray of oncogenes, protooncogenes, and suppressor genes is produced using cDNA or cRNA from mRNA isolated by the method herein.

0.4 to 1 mg of nuclear poly (A) RNA is isolated from normal breast calls as well as breast cancer cells. Fluorescently labeled cDNA is produced using the FAIRPLAY MIROARRAY LABELING KIT (Stratagene, La Jolla, Calif.). The labeled cDNA is hybridized to the above microarray and differentially expressed genes identified.

Example 13

Use of the Method for Producing a cDNA Library cDNA libraries are used to isolate homologs or full-length clones of genes using a probe. During the isolation of homologs, the identification of various sized transcripts which are expressed from a single gene are identified. If the mRNA used to produce the library contains mRNA degradation products, the library will be less likely to provide full-length clones and may give erroneous information about alternate transcripts for a gene of interest. Thus, to produce a cDNA library for the illness bipolar disorder, the following protocol is followed: Cerebrospinal fluid (CSF) from a patient with bipolar disorder is isolated and the cellular components used to isolate nuclear mRNA as in Examples 1-4. The mRNA is used to produce a cDNA library following the instructions in the LAMBDA ZAP-cDNA SYNTHESIS KIT and using a LAMBDA ZAP II vector (Stratagene, La Jolla, Calif.) to produce the library.

Example 14

Use of the Method to Identify Differentially Expressed Gene Products with the CASTAWAY SYSTEM There are a wide range of methods and kits available for the identification of differentially expressed gene products. One general problem with these methods is the use of total RNA or mRNA from whole cells or tissues for the analysis. This leads to inprecise and sometimes incorrect results. Although the method described herein can be used for any of these systems, the RAP-PCR system was chosen as a prototype and the Stratagene CASTAWAY precast gels (Stratagene Cloning Systems, Inc., La Jolla Calif.) chosen for fast analysis of the results.

A human myelomonocytic cell line (HL60) is stimulated for 4 hours with phorbol myristate acetate (PMA). Arbitrary primers are used for the first-strand synthesis from nuclear RNA as isolated in Examples 1-4. PCR amplification of the reverse transcribed nuclear mRNA is conducted. The PCR products are run on the CASTAWAY system as outlined in the Stratagene manual. The pattern of PCR bands is compared to the pattern from a nonstimulated control. A number of unique bands are identified, isolated from the gel and reamplified by PCR for further analysis. A Northern blot is run using mRNA from the nuclear fractions of stimulated and nonstimulated cells to verify the results.

Example 15

Method of Quantitation of DNA Repair Function and its Applications

The method involves stimulating the cells with a DNA damaging agent, preparing nuclear RNA or mRNA, and quantitating the levels of newly expressed genes. Without the nuclear mRNA methodology disclosed herein, conventional methods cannot identify the increase in specific gene expression because of enhanced degradation in the cytosol. Thus, the method uses the mRNA isolation method disclosed herein (see Examples 1 and 2).

The stimulation may be in vitro in tissue culture or a test tube, in vivo by using whole body stimulation. Any type of cell may be used for the method, however, typical cells include whole blood, blood leukocytes, biopsy specimens, surgically removed specimens, hair follicles, lavage, exudates, whole body, etc.

The cells are damaged with a DNA damaging agent including, but not restricted to: radioactivity, ultraviolet irradiation, X-rays, chemicals, ultrasound, food, cosmetics, environmental agents, stress, chemical mutagens, toxins, etc.

After damaging the cells with a DNA damaging agent, the nuclear mRNA is prepared by the method outlined in Examples 1-4. Gene expression is quantitated by Northern blot, RNase protection assay, sandwich hybridization assay, gene amplification (PCR, "real time PCR, LCR, NASBA, sDNA, bDNA, invader , etc.) real time PCR includes TAQMAN, MOLECULAR BEACON, AMPLIFLUOR, SCORPION, SYBR-DYE, POLICEMAN, etc. Typically, cells which have been damaged with a certain agent are compared to cells which have not been damaged.

In this way genes which are activated or up-regulated by DNA damage are identified. Newly expressed genes include genes responsible for the DNA repair mechanism, genes responsible for apoptosis, and genes of unknown function.

Genes that are known to be responsive to the DNA repair mechanism include p53, p21, DNA polymerases, etc. Genes which are known to be responsive to apoptosis include caspases, BAX, bcl-2, etc. These can be used as controls to make sure the method is working. However, of major interest are genes involved in these processes which have not been identified as having this role before.

Genes of unknown function include genes discovered by DNA microarray chip, subtraction hybridization, differential display, etc. These genes may be analyzed by database to find homologs and active sites. However, the function is best identified by in vitro methods.

Applications for the genes identified include the following: Screening of high risk individuals for cancer, Drug screening for a cancer-preventative compound (ie: a medicine, herb, food, etc.), assessment of aging, monitoring of health and disease, identification of non-cancer inducing products (food, cosmetics, drugs, perfume, etc). Screening may be performed by genechip or array technology.

Thus, the method described here is very rapid and sensitive for "true" gene expression analysis, which represents transcription without degradation products. In addition, the method is adaptable to high throughput automation systems using commercially available instruments. It is likely that nuclear gene expression analysis will become a standard method of gene expression analysis in the future.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method for detecting gene expression in a cell nucleus, comprising:

trapping a cell on a filter or a membrane that does not retain cytoplasmic RNA when washed with solutions that do not lyse cell nuclei, said cell having a cell membrane and a nuclear membrane;

contacting the cell with a cell membrane permeation solution thereby increasing permeability of the cell membrane without increasing permeability of the nuclear membrane, wherein the membrane permeation solution is at room temperature;

washing away cytoplasmic mRNA by vacuum filtration, thereby obtaining the cell nucleus on the filter or membrane;

contacting the cell nucleus with a lysis buffer while the cell nucleus is still on the filter or membrane, thereby permeabilizing the nucleus without damage to mRNA within the nucleus, and obtaining a nuclear solution;

recovering the mRNA from the nuclear solution; and determining gene expression in the cell based on the quantity of at least one specific recovered mRNA.

2. The method according to claim 1, wherein said filter or membrane is a glass fiber membrane.

3. The method according to claim 1, wherein said cell membrane permeation solution is a mild detergent which lyses the cell membrane but does not lyse the nucleus.

4. The method according to claim 1, wherein the washing is conducted on the filter or membrane.

5. The method according to claim 1, wherein said lysis buffer comprises a strong detergent.

6. The method according to claim 1, wherein the mRNA recovery step is conducted by transferring the nuclear solution to an oligo dT-immobilized solid support.

7. The method according to claim 6, wherein the solid support is a plate, a filter or a column.

8. The method according to claim 1, wherein the mRNA recovery step is conducted by transferring the nuclear solution to an oligonucleotides-immobilized solid support, said oligonucleotides having a sequence complimentary to the mRNA.

9. A method for determining a gene expression in cell nuclei, comprising:

(a) collecting cells from a first biological sample, said cells having a cell membrane and a nuclear membrane;

(b) trapping the cells on a filter or a membrane that does not retain cytoplasmic RNA when washed with solutions that do not lyse cell nuclei;

(c) contacting the cells with a cell membrane permeation solution to increase permeability of the cell membranes, without increasing permeability of the nuclear membrane, wherein the membrane permeation solution is at room temperature;

(d) washing away cytoplasmic mRNA released from said cells by vacuum filtration or centrifugation, thereby obtaining the cell nucleus on the filter or membrane;

(e) contacting the cytoplasm-washed cells with a cell dissolving solution to dissolve the nuclei while the cell nucleus is still on the filter or membrane, thereby obtaining a nucleus solution without damage to the mRNA within the nucleus;

(f) recovering mRNA from the nucleus solution;

(g) repeating steps (a) through (f) using cells from a second biological sample; and (h) determining gene expression in the cells based on a change in the quantities of the mRNA recovered in steps (f) and (g), respectively.

10. The method according to claim 9, wherein a designated treatment has been applied to the second sample, not the first sample.

11. A method for the isolation of nuclear RNA from a cell, comprising:

trapping cells on a filter or a membrane that does not retain cytoplasmic RNA when washed with solutions that do not lyse cell nuclei, said cells having a cell membrane and a nuclear membrane;

permeabilizing the cells at room temperature without increasing permeability of the nuclear membranes and isolating cell nuclei on the filter or membrane by vacuum filtration or centrifugation of cytosol; and dissolving membranes of said cell nuclei while the cell nucleus is still on the filter or membrane thereby obtaining permeabilized contents of the nuclei; and recovering the nuclear RNA.

12. The method according to claim 11, wherein said filter or membrane is a glass fiber membrane.

13. The method according to claim 11, wherein said permeabilizing is by applying a mild detergent.

14. The method according to claim 11, wherein said dissolving the nuclear membrane is by a lysis buffer.

15. The method according to claim 14, wherein said lysis buffer comprises a strong detergent.

16. The method according to claim 11, wherein said recovering of said nuclear RNA is by transferring the permeabilized contents of the nuclei to an oligo dT plate, filter or column.

17. A method for the identification and/or quantitation of transcripts of a specific gene, comprising:

isolating RNA from the nuclei of cells by a method comprising the following steps:

trapping the cells on a filter or a membrane that does not retain cytoplasmic RNA when washed with solutions that do not lyse cell nuclei;

permeabilizing the cells at room temperature and isolating nuclei from the cells by vacuum filtration or centrifugation, without permeabilizing the nuclei, such that said nuclei remain on said filter or membrane; and dissolving the nuclear membrane on said filter or membrane, without damage to RNA within the nucleus, thereby obtaining permeabilized contents of the nuclei; and recovering nuclear RNA on a second filter or membrane or a plate;

reverse transcribing the nuclear RNA on the second filter or membrane or a plate; and performing PCR using primers specific for the gene, thereby identifying and/or quantifying the transcripts of said gene.

18. A method for the identification or quantitation of genes involved in the DNA repair process, comprising:

treating cells with a DNA damaging agent;

isolating nuclear RNA by the method of claim 11;

reverse transcribing the mRNA;

comparing genes in the cells treated with the damaging agent to genes in cells untreated with the damaging agent; and identifying genes in which transcription has been up-regulated or activated by the DNA damage.

19. The method according to claim 18, wherein said identifying is by a method selected from the group consisting of: reverse transcription polymerase chain reaction (RT-PCR), random arbitrarily primed PCR (RAP PCR), differential display PCR (ddPCR), subtraction, and array or genechip analysis.

20. A method for the identification or quantitation of genes involved in the DNA repair process, comprising:

treating cells with a DNA damaging agent;

isolating nuclear RNA by the method of claim 11;

comparing genes in the cells treated with the damaging agent to genes in cells untreated with the damaging agent; and identifying genes in which transcription has been up-regulated or activated by the DNA damage by using a Northern blot method.

* * * * *

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: mitochondrial DNA forward primer

<400> SEQUENCE: 1
tccacactag cagagaccaa ccg                                              23

<210> SEQ ID NO 2
<211> LENGTH: 25
<212> TYPE: DNA
<213> ORGANISM: Artificial Sequence
<220> FEATURE:
<223> OTHER INFORMATION: mitochondrial DNA reverse primer

<400> SEQUENCE: 2
agaacaggga ggttagaagt agggt                                            25

<210> SEQ ID NO 3
<211> LENGTH: 20
<212> TYPE: DNA
<213> ORGANISM: Artificial Sequence
<220> FEATURE:
<223> OTHER INFORMATION: Beta actin forward primer

<400> SEQUENCE: 3
tggcaccaca ccttctacaa                                                  20

<210> SEQ ID NO 4
<211> LENGTH: 20
<212> TYPE: DNA
<213> ORGANISM: Artificial Sequence
<220> FEATURE:
<223> OTHER INFORMATION: Beta actin reverse primer

<400> SEQUENCE: 4
catctcttgc tcgaagtcca                                                  20

<210> SEQ ID NO 5
<211> LENGTH: 23
<212> TYPE: DNA
<213> ORGANISM: Artificial Sequence
<220> FEATURE:
<223> OTHER INFORMATION: Beta actin intron forward primer

<400> SEQUENCE: 5
gtgctgtgga agctaagtcc tgc                                              23

<210> SEQ ID NO 6
<211> LENGTH: 25
<212> TYPE: DNA
<213> ORGANISM: Artificial Sequence
<220> FEATURE:
<223> OTHER INFORMATION: Beta actin intron reverse primer

<400> SEQUENCE: 6
cacccacctt gatcttcatt gtgct                                            25

<210> SEQ ID NO 7
<211> LENGTH: 24

```
<212> TYPE: DNA
<213> ORGANISM: Artificial Sequence
<220> FEATURE:
<223> OTHER INFORMATION: jun-B forward primer

<400> SEQUENCE: 7
aggacaaggt gaagacgctc aagg                                              24

<210> SEQ ID NO 8
<211> LENGTH: 20
<212> TYPE: DNA
<213> ORGANISM: Artificial Sequence
<220> FEATURE:
<223> OTHER INFORMATION: jun-B reverse primer

<400> SEQUENCE: 8 gcagggacg ttcagaaggc                                                    20

<210> SEQ ID NO 9
<211> LENGTH: 24
<212> TYPE: DNA
<213> ORGANISM: Artificial Sequence
<220> FEATURE:
<223> OTHER INFORMATION: p21 forward primer

<400> SEQUENCE: 9
ccgctctaca tcttctgcct tagt                                              24

<210> SEQ ID NO 10
<211> LENGTH: 28
<212> TYPE: DNA
<213> ORGANISM: Artificial Sequence
<220> FEATURE:
<223> OTHER INFORMATION: p21 reverse primer

<400> SEQUENCE: 10
cagcactctt aggaacctct cattcaac                                          28
```